United States Patent
Collier et al.

(10) Patent No.: US 10,604,690 B2
(45) Date of Patent: Mar. 31, 2020

(54) COMPOSITION INCLUDING 2,3,3,3-TETRAFLUOROPROPENE

(71) Applicant: ARKEMA FRANCE, Colombes (FR)

(72) Inventors: Bertrand Collier, Saint Genis Laval (FR); Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/481,815

(22) Filed: Apr. 7, 2017

(65) Prior Publication Data
US 2017/0210962 A1 Jul. 27, 2017

Related U.S. Application Data

(63) Continuation of application No. 14/651,855, filed as application No. PCT/FR2013/052977 on Dec. 6, 2013, now Pat. No. 9,650,551.

(30) Foreign Application Priority Data

Dec. 26, 2012 (FR) .................... 12.62766

(51) Int. Cl.
 *C09K 5/04* (2006.01)
 *C09K 5/08* (2006.01)
 (Continued)

(52) U.S. Cl.
 CPC ............... *C09K 5/08* (2013.01); *C07C 21/18* (2013.01); *C09K 3/00* (2013.01); *C09K 5/044* (2013.01);
 (Continued)

(58) Field of Classification Search
 CPC .............. C09K 2205/126; C09K 5/044; C09K 2205/122
 See application file for complete search history.

(56) References Cited

U.S. PATENT DOCUMENTS

| 2,931,840 A | 4/1960 | Marquis |
| 8,070,977 B2 | 12/2011 | Rached |

(Continued)

FOREIGN PATENT DOCUMENTS

| WO | WO 2007/056128 A1 | 5/2007 |
| WO | WO 2010/001025 A2 | 1/2010 |

(Continued)

OTHER PUBLICATIONS

U.S. Appl. No. 13/128,996, Wissam Rached, filed May 12, 2011, (Cited herein as US Patent Application Publication No. 2011/0219791 A1 of Sep. 15, 2011).

(Continued)

*Primary Examiner* — John R Hardee
(74) *Attorney, Agent, or Firm* — Buchanan Ingersoll & Rooney P.C.

(57) ABSTRACT

A composition including the compound HFO-1234yf and at least one other, additional, compound selected from HCFC-240db, HCFO-1233xf, HCFC-243db, HCFO-1233zd, HCC-40, HCFC-114a, HCFC-115, HCFC-122, HCFC-23, HCFC-124, HCFC-124a, HFC-125, HCFC-133a, HCFC-142, HCFC-143, HFC-52a, HCFC-243ab, HCFC-244eb, HFC-281ea, HCO-1110, HCFO-1111, HCFO-1113, HCFO-1223xd, and HCFO-1224xe. A composition including the compound HFO-1234yf and at least two compounds selected from HFO-1234ze, HFC-245cb, HFC-134a, HCFC-115, HFC-152a, HCC-40 and HFO-1243zf.

8 Claims, 1 Drawing Sheet

(51) Int. Cl.
*C09K 3/00* (2006.01)
*H01B 3/56* (2006.01)
*C07C 21/18* (2006.01)

(52) U.S. Cl.
CPC .............. *C09K 5/045* (2013.01); *H01B 3/56* (2013.01); *C09K 2205/122* (2013.01); *C09K 2205/126* (2013.01); *C09K 2205/22* (2013.01); *C09K 2205/32* (2013.01)

(56) References Cited

U.S. PATENT DOCUMENTS

| | | | |
|---|---|---|---|
| 8,075,798 | B2 | 12/2011 | Rached |
| 8,246,850 | B2 | 8/2012 | Rached |
| 8,252,198 | B2 | 8/2012 | Rached |
| 8,557,135 | B2 | 10/2013 | Rached |
| 8,808,569 | B2 | 8/2014 | Rached |
| 8,858,824 | B2 | 10/2014 | Boussand |
| 8,858,825 | B2 | 10/2014 | Guerin et al. |
| 9,011,711 | B2 | 4/2015 | Rached |
| 9,028,706 | B2 | 5/2015 | Rached et al. |
| 9,039,922 | B2 | 5/2015 | Rached |
| 9,127,191 | B2 | 9/2015 | Rached |
| 9,133,379 | B2 | 9/2015 | Rached |
| 9,175,203 | B2 | 11/2015 | Rached |
| 9,267,064 | B2 | 2/2016 | Rached |
| 9,315,708 | B2 | 4/2016 | Guerin et al. |
| 9,399,726 | B2 | 7/2016 | Rached |
| 9,505,968 | B2 | 11/2016 | Rached |
| 9,512,343 | B2 | 12/2016 | Rached et al. |
| 9,599,381 | B2 | 3/2017 | Rached |
| 9,650,551 | B2 | 5/2017 | Collier et al. |
| 9,650,553 | B2 | 5/2017 | Deur-Bert et al. |
| 9,651,551 | B2 | 5/2017 | Collier et al. |
| 9,663,697 | B2 | 5/2017 | Rached |
| 9,676,984 | B2 | 6/2017 | Guerin et al. |
| 9,683,155 | B2 | 6/2017 | Deur-Bert et al. |
| 9,683,157 | B2 | 6/2017 | Rached |
| 9,884,984 | B2 | 2/2018 | Rached |
| 9,908,828 | B2 | 3/2018 | Rached et al. |
| 9,969,918 | B2 | 5/2018 | Deur-Bert et al. |
| 10,023,780 | B2 | 7/2018 | Guerin et al. |
| 10,035,938 | B2 | 7/2018 | Rached |
| 10,119,055 | B2 | 11/2018 | Boussand |
| 10,125,296 | B2 | 11/2018 | Rached |
| 10,131,829 | B2 | 11/2018 | Deur-Bert et al. |
| 10,252,913 | B2 | 4/2019 | Bonnet et al. |
| 10,316,231 | B2 | 6/2019 | Rached |
| 10,358,592 | B2 | 7/2019 | Rached |
| 10,377,935 | B2 | 8/2019 | Guerin et al. |
| 10,399,918 | B2 | 9/2019 | Rached |
| 2007/0112227 | A1 | 5/2007 | Mukhopadhyay et al. |
| 2007/0112229 | A1 | 5/2007 | Mukhopadhyay et al. |
| 2009/0253946 | A1 | 10/2009 | Van Der Puy |
| 2011/0031436 | A1 | 2/2011 | Mahler et al. |
| 2011/0084228 | A1 | 4/2011 | Rached |
| 2011/0095224 | A1 | 4/2011 | Rached |
| 2011/0105809 | A1 | 5/2011 | Devic et al. |
| 2011/0186772 | A1 | 8/2011 | Rached |
| 2011/0219791 | A1 | 9/2011 | Rached |
| 2011/0219792 | A1 | 9/2011 | Rached |
| 2011/0240254 | A1 | 10/2011 | Rached |
| 2011/0284181 | A1 | 11/2011 | Rached |
| 2011/0312101 | A1* | 12/2011 | Tsuchiya ................ C09K 5/045 436/101 |
| 2012/0041239 | A1* | 2/2012 | Suzuki ................ C07C 17/206 570/160 |
| 2012/0049104 | A1 | 3/2012 | Rached |
| 2012/0056123 | A1 | 3/2012 | Rached |
| 2012/0065437 | A1* | 3/2012 | Merkel ................ B01J 27/10 570/175 |
| 2012/0068105 | A1 | 3/2012 | Rached et al. |
| 2012/0126187 | A1* | 5/2012 | Low ................ C11D 7/5009 252/602 |
| 2012/0144857 | A1 | 6/2012 | Rached |
| 2012/0151958 | A1 | 6/2012 | Rached |
| 2012/0151959 | A1 | 6/2012 | Rached |
| 2012/0153213 | A1 | 6/2012 | Rached |
| 2012/0159982 | A1 | 6/2012 | Rached |
| 2012/0161064 | A1 | 6/2012 | Rached |
| 2012/0167615 | A1 | 7/2012 | Rached |
| 2012/0205574 | A1 | 8/2012 | Rached et al. |
| 2013/0092869 | A1 | 4/2013 | Boussand |
| 2013/0105724 | A1 | 5/2013 | Boussand |
| 2013/0186114 | A1 | 7/2013 | Guerin et al. |
| 2014/0008565 | A1 | 1/2014 | Rached et al. |
| 2014/0031597 | A1 | 1/2014 | Deur-Bert et al. |
| 2014/0075969 | A1 | 3/2014 | Guerin et al. |
| 2014/0318160 | A1 | 10/2014 | Rached |
| 2014/0326017 | A1 | 11/2014 | Rached |
| 2015/0008357 | A1 | 1/2015 | Furuta et al. |
| 2015/0027146 | A1 | 1/2015 | Boussand |
| 2015/0152306 | A1 | 6/2015 | Rached |
| 2015/0152307 | A1 | 6/2015 | Rached |
| 2015/0322317 | A1 | 11/2015 | Collier et al. |
| 2015/0322321 | A1 | 11/2015 | Deur-Bert et al. |
| 2015/0344761 | A1 | 12/2015 | Rached |
| 2015/0353799 | A1 | 12/2015 | Deur-Bert et al. |
| 2015/0353802 | A1 | 12/2015 | Rached |
| 2015/0376486 | A1* | 12/2015 | Hashimoto ............ C09K 5/045 252/67 |
| 2016/0009555 | A1 | 1/2016 | Bonnet et al. |
| 2016/0024363 | A1 | 1/2016 | Rached |
| 2016/0025394 | A1 | 1/2016 | Rached |
| 2016/0115361 | A1 | 4/2016 | Boussand |
| 2016/0122609 | A1 | 5/2016 | Rached |
| 2016/0194541 | A1 | 7/2016 | Guerin et al. |
| 2016/0244652 | A1 | 8/2016 | Rached |
| 2016/0272561 | A1 | 9/2016 | Rached et al. |
| 2016/0298014 | A1 | 10/2016 | Rached |
| 2016/0355718 | A1 | 12/2016 | Rached |
| 2016/0376484 | A1 | 12/2016 | Guerin et al. |
| 2017/0037291 | A1 | 2/2017 | Rached et al. |
| 2017/0080773 | A1 | 3/2017 | Rached |
| 2017/0145276 | A1 | 5/2017 | Rached |
| 2017/0210960 | A1 | 7/2017 | Deur-Bert et al. |
| 2017/0218241 | A1 | 8/2017 | Deur-Bert et al. |
| 2017/0218242 | A1 | 8/2017 | Rached |
| 2018/0086173 | A1 | 3/2018 | Rached |
| 2018/0134936 | A1 | 5/2018 | Rached |
| 2018/0148395 | A1 | 5/2018 | Rached et al. |
| 2018/0244970 | A1 | 8/2018 | Rached |
| 2018/0282603 | A1 | 10/2018 | Guerin |
| 2018/0327645 | A1 | 11/2018 | Boussand |
| 2019/0023957 | A1 | 1/2019 | Rached |
| 2019/0203094 | A1 | 7/2019 | Rached |
| 2019/0249057 | A1 | 8/2019 | Rached |
| 2019/0284500 | A1 | 9/2019 | Rached |

FOREIGN PATENT DOCUMENTS

| WO | WO 2011/163117 A1 | 12/2011 |
|---|---|---|
| WO | WO 2012/098420 A1 | 7/2012 |
| WO | WO 2013/154059 A1 | 10/2013 |

OTHER PUBLICATIONS

U.S. Appl. No. 13/129,240, Wissam Rached, filed May 13, 2011, (Cited herein as US Patent Application Publication No. 2011/0219792 A1 of Sep. 15, 2011).

U.S. Appl. No. 13/146,721, Wissam Rached, filed Jul. 28, 2011, (Cited herein as US Patent Application Publication No. 2011/0284181 A1 of Nov. 24, 2011).

U.S. Appl. No. 13/808,326, Béatrice Boussand, filed Jan 4, 2013, (Cited herein as US Patent Application Publication No. 2013/0105724 A1 of May 2, 2013).

U.S. Appl. No. 14/371,118, Béatrice Boussand, filed Jul. 8, 2014, (Cited herein as US Patent Application Publication No. 2015/0027146 A1 of Jan. 29, 2015).

U.S. Appl. No. 14/615,780, Wissam Rached, filed Feb. 6, 2015, (Cited herein as US Patent Application Publication No. 2015/0152307 A1 of Jun. 4, 2015).

(56) References Cited

OTHER PUBLICATIONS

U.S. Appl. No. 14/830,130, Wissam Rached, filed Aug. 19, 2015, (Cited herein as US Patent Application Publication No. 2015/0353802 a1 of Dec. 10, 2015).
U.S. Appl. No. 14/772,950, Phillippe Bonnet, filed Sep. 4, 2015, (Cited herein as US Patent Application Publication No. 2016/0009555 A1 of Jan. 14, 2016).
U.S. Appl. No. 14/990,159, Béatrice Boussand, filed Jan. 7, 2016, (Cited herein as US Patent Application Publication No. 2016/0115361 A1 of Apr. 28, 2016).
U.S. Appl. No. 14/992,387, Wissam Rached, filed Jan. 11, 2016, (Cited herein as US Patent Application Publication No. 2016/0122609 A1 of May 5, 2016).
U.S. Appl. No. 15/073,108, Wissam Rached, filed Mar. 17, 2016, (Cited herein as US Patent Application Publication No. 2016/0272561 A1 of Sep. 22, 2016).
U.S. Appl. No. 15/238,883, Wissam Rached, filed Aug. 17, 2016, (Cited herein as US Patent Application Publication No. 2016/0355718 A1 of Dec. 8, 2016).
U.S. Appl. No. 14/903,461, Sophie Guerin, filed Jan. 7, 2016, (Cited herein as US Patent Application Publication No. 2016/0376484 A1 of Dec. 29, 2016).
U.S. Appl. No. 15/297,569, Wissam Rached, filed Oct. 19, 2016, (Cited herein as US Patent Application Publication No. 2017/0037291 A1 Feb. 9, 2017).
U.S. Appl. No. 15/368,347, Wissam Rached, filed Dec. 2, 2016, (Cited herein as US Patent Application Publication No. 2017/0080773 A1 of Mar. 23, 2017).
U.S. Appl. No. 15/396,855, Wissam Rached, filed Jan. 3, 2017, (Cited herein as US Patent Application Publication No. 2017/0145276 A1 of May 25, 2017).
U.S. Appl. No. 15/481,873, Dominique Deur-Bert, filed Apr. 7, 2017, (Cited herein as US Patent Application Publication No. 2017/0210960 A1 of Jul. 27, 2017).
U.S. Appl. No. 15/490,541, Dominique Deur-Bert, filed Apr. 18, 2017 (Cited herein as US Patent Application Publication No. 2017/0218241 A1 of Aug. 3, 2017).
U.S. Appl. No. 15/491,717, Wissam Rached, filed Apr. 19, 2017 (Cited herein as US Patent Application Publication No. 2017/0218242 A1 of Aug. 3, 2017).
International Search Report (PCT/ISA/210) dated Apr. 9, 20147 in PCT/FR2013/052977, 4 pages, European Patent Office, Rijswjk, NL (English and French Language versions).
U.S. Appl. No. 15/809,164, Wissam Rached, filed Nov. 10, 2017, (Cited herein as US Patent Application Publication No. 2018/0086173 A1 of Mar. 29, 2018).
U.S. Appl. No. 15/820,996, Wissam Rached, filed Nov. 22, 2017.
U.S. Appl. No. 15/856,703, Wissam Rached, filed Dec. 28, 2017, (Cited herein as US Patent Application Publication No. 2018/0134936 A1 of May 17, 2018).
U.S. Appl. No. 15/878,794, Wissam Rached, Sophie Guerin and Pascale Kindler, filed Jan. 24, 2018, (Cited herein as US Patent Application Publication No. 2018/0148395 A1 of May 31, 2018).
U.S. Appl. No. 15/997,077, Sophie Guerin and Wissam Rached, filed Jun. 4, 2018.
U.S. Appl. No. 16/034,539, Béatrice Boussand, filed Jul. 13, 2018.
Rached, Wissam, U.S. Appl. No. 15/820,996 entitled "Method for Heating and/or Air Conditioning a Vehicle,"filed in the U.S. Patent and Trademark Office filed Nov. 22, 2017.
Guerin, Sophie, et al., U.S. Appl. No. 15/997,077 entitled "2,3,3,3-Tetrafluoropropene Compositions Having Improved Miscibility," filed in the U.S. Patent and Trademark Office filed Jun. 4, 2018.
Boussand, Beatrice, U.S. Appl. No. 16/034,539 entitled "Stable 2,3,3,3-Tetrafluoropropene Composition," filed in the U.S. Patent and Trademark Office filed Jul. 13, 2018.
Rached, Wissam, U.S. Appl. No. 16/142,492 entitled "Heat Transfer Fluid," filed in the U.S. Patent and Trademark Office filed Sep. 26, 2018.
Rached, Wissam, U.S. Appl. No. 16/143,518 entitled "Binary Refrigerating Fluid," filed in the U.S. Patent and Trademark Office filed Sep. 27, 2018.
Rached, Wissam, U.S. Appl. No. 16/339,903 entitled "Tetrafluoropropene-Based Azeotropic Compositions, " filed in the U.S. Patent and Trademark Office filed Apr. 5, 2019.
Rached, Wissam, U.S. Appl. No. 16/339,956 entitled "Use of Tetrafluoropropene Based Compositions", filed in the U.S. Patent and Trademark Office filed Apr. 5, 2019.
Rached, Wissam, U.S. Appl. No. 16/395,413 entitled "Low-Temperature and Average-Temperature Refrigeration," filed in the U.S. Patent and Trademark Office filed Apr. 26, 2019.
Rached, Wissam, U.S. Appl. No. 16/477,263 entitled "Composition Comprising 2,3,3,3-Tetrafluoropropene," filed in the U.S. Patent and Trademark Office filed Jul. 11, 2019.
Rached, Wissam, U.S. Appl. No. 16/477,318 entitled "Composition Comprising 2,3,3,3-Tetrafluoropropene," filed in the U.S. Patent and Trademark Office filed Jul. 11, 2019.
Rached, Wissam, et al., U.S. Appl. No. 16/514,241 entitled "Stabilization of 1-Chloro-3,3,3-Trifluoropropene," filed in the U.S. Patent and Trademark Office filed Jul. 17, 2019.

\* cited by examiner

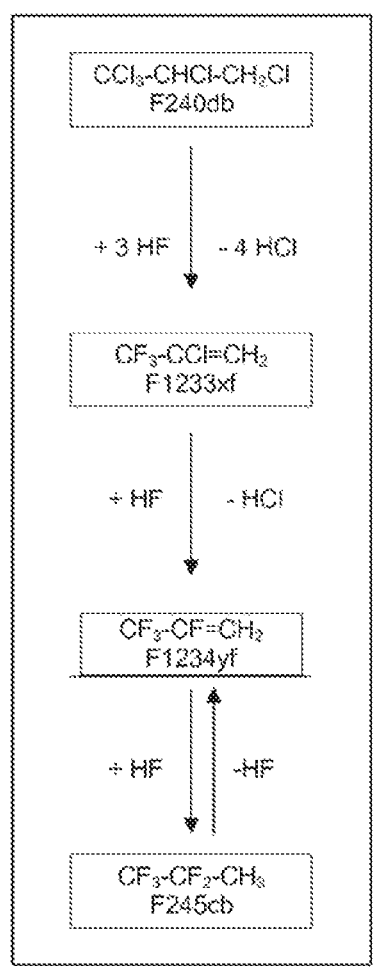

COMPOSITION INCLUDING 2,3,3,3-TETRAFLUOROPROPENE

CROSS REFERENCE TO RELATED APPLICATIONS

The present application is a continuation of U.S. application Ser. No. 14/651,855, filed on Jun. 12, 2015, which is a U.S. national phase application of International Application No. PCT/FR2013/052977, filed on Dec. 6, 2013, claims the benefit of French Application No. 12.62766, filed on Dec. 26, 2012. The entire contents of each of U.S. application Ser. No. 14/651,855, International Application No. PCT/FR2013/052977, French Application No. 12.62766, are hereby incorporated herein by reference in their entirety.

TECHNICAL FIELD

The present invention relates to compositions comprising 2,3,3,3-tetrafluoropropene, which are of use in many fields of application such as refrigeration, blowing agents, solvents and aerosols.

SUMMARY

One very important parameter in the choice of a composition of use in the fields of refrigeration, air conditioning and heat pumps is its impact on the environment.

The manufacture of 2,3,3,3-tetrafluoropropene (HFO-1234yf), being accompanied by a multitude of by-products having a boiling point close to HFO-1234yf, results in quite complex and expensive purification steps. The difficulty encountered during the purification of HFO-1234yf generally involves a consequent loss of desired product. Furthermore, these by-products may form binary or tertiary azeotropic compositions with HFO-1234yf, rendering the separation by simple distillation impossible.

DRAWING

FIG. 1 illustrates a series of reactions to obtain a composition according to an embodiment of the invention.

DETAILED DESCRIPTION

One subject of the present invention is a composition comprising the compound HFO-1234yf and at least one other additional compound chosen from HCFC-240db, HCFO-1233xf, HCFC-243db, HCFO-1233zd, HCC-40, HCFC-114a, HCFC-115, HCFC-122, HCFC-123, HCFC-124, HCFC-124a, HFC-125, HCFC-133a, HCFC-142, HCFC-143, HFC-152a, HCFC-243ab, HCFC-244eb, HFC-281ea, HCO-1110, HCFO-1111, HCFO-1113, HCFO-1223xd and HCFO-1224xe.

Preferably, all of the additional compounds represents at most 1% by weight of the composition comprising the HFO-1234yf and advantageously at most 0.5% by weight.

Compounds such as HCFC-115, HFC-152a and HCC-40 have a boiling point particularly close to that of HFO-1234yf.

According to one embodiment of the invention, the composition comprises the compound HFO-1234yf and at least one other additional compound chosen from HCFC-115, HFC-152a and HCC-40, preferably HFC-152a and/or HCC-40.

Advantageously, the HCFC-115 and/or HFC-152a and/or HCC-40 when it (they) is (are) present in the composition, represent(s) at most 500 ppm and particularly preferably represent(s) at most 50 ppm.

According to this embodiment, the composition may additionally comprise at least one compound chosen from HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd and HCFO-1224xe.

In one embodiment, the composition according to the invention may also comprise at least one compound chosen from HFO-1234ze, HFC-245cb, HFC-245eb, HFC-245fa, HFC-23, HFC-134a, HFC-143a, HFC-236fa, HCFC-244bb, HCFC-244db, HFO-1132a, HFO-1223, HFO-1225zc, HFO-1225ye, HCFO-1232xf and HFO-1243zf.

Irrespective of the embodiment, all of the additional compound(s) represents at most 1% by weight of the composition comprising the HFO-1234yf and advantageously at most 0.5% by weight.

By way of example, mention may especially be made of the following compounds, the acronyms of which represent:

HCFC-240db: 1,1,1,2,3-pentachloropropane or $CCl_3$—$CHCl$—$CH_2Cl$

HCFO-1233xf: 3,3,3-trifluoro-2-chloropropene or $CF_3$—$CCl$=$CH_2$

HCFC-243db: 1,1,1-trifluoro-2,3-dichloropropane or $CF_3$—$CHCl$—$CH_2Cl$

HCFO-1233zd: E/Z-3,3,3-trifluoro-1-chloropropene or $CF_3$—$CH$=$CHCl$

HCC-40: chloromethane or $CH_3Cl$

HCFC-114a: 1,1,1,2-tetrafluoro-2,2-dichloroethane or $CF_3$—$CCl_2F$

HCFC-115: 1,1,1,2,2-pentafluoro-2-chloroethane $CF_3$—$CClF_2$

HCFC-122: 1,1,2-trichloro-2,2-difluoroethane or $CHCl_2$—$CClF_2$

HCFC-123: 1,1,1-trifluoro-2,2-dichloroethane or $CF_3$—$CHCl_2$

HCFC-124: 1,1,1,2-tetrafluoro-2-chloroethane or $CF_3$—$CHClF$

HCFC-124a: 1,1,2,2,-tetrafluoro-2-chloroethane or $CHF_2$—$CClF_2$

HFC-125: 1,1,1,2,2,-pentafluoroethane or $CF_3$—$CHF_2$

HCFC-133a: 1,1,1-trifluoro-2-chloroethane or $CF_3$—$CH_2Cl$

HCFC-142: 1,1-difluoro-2-chloroethane or $CHF_2$—$CH_2Cl$

HCFC-143: 1,1,2-trifluoroethane or $CHF_2$—$CH_2F$

HFC-152a: 1,1-difluoroethane or $CHF_2$—$CH_3$

HCFC-243ab: 1,1,1-trifluoro-2,2-dichloropropane or $CF_3$—$CCl_2$—$CH_3$

HCFC-244eb: 1,1,1,2-tetrafluoro-3-chloropropane or $CF_3$—$CHF$—$CH_2Cl$

HFC-281ea: 2-fluoropropane or $CH_3$—$CFH$—$CH_3$

HCO-1110: 1,1,2,2-tetrachloroethylene or $CCl_2$=$CCl_2$

HCFO-1111: 1,1,2-trichloro-2-fluoroethylene or $CCl_2$=$CClF$

HCFO-1113: 1,1,2-trifluoro-2-chloroethylene or $CF_2$=$CClF$

HCFO-1223xd: E/Z-3,3,3-trifluoro-1,2-dichloropropene or $CF_3$—$CCl$=$CHCl$

HCFO-1224xe: E/Z-1,3,3,3-tetrafluoro-2-chloropropene or $CF_3$—$CCl$=$CHF$

HFO-1234ze: E/Z-1,3,3,3-tetrafluoropropene or $CF_3$—CH=CHF

HFC-245cb: 1,1,1,2,2-pentafluoropropane or $CF_3$—$CF_2$—$CH_3$

HFC-245eb: 1,1,1,2,3-pentafluoropropane or $CF_3$—CHF—$CH_2F$

HFC-245fa: 1,1,1,3,3-pentafluoropropane or $CF_3$—$CH_2$—$CHF_2$

HFC-23: trifluoromethane or $CHF_3$

HFC-134a: 1,1,1,2-tetrafluoroethane or $CF_3$—$CH_2F$

HFC-143a: 1,1,1-trifluoroethane or $CF_3$—$CH_3$

HFC-236fa: 1,1,1,3,3,3-hexafluoropropane or $CF_3$—$CH_2$—$CF_3$

HCFC-244bb: 1,1,1,2-tetrafluoro-2-chloropropane or $CF_3$—CFCl—$CH_3$

HCFC-244db: 1,1,1,3-tetrafluoro-2-chloropropane or $CF_3$—CHCl—$CH_2F$

HFO-1132a: 1,2-difluoroethylene or CHF=CHF

HFO-1223: 3,3,3-trifluoropropyne or $CF_3$—CECH

HFO-1225zc: E/Z-1,1,3,3,3-pentafluoropropene or $CF_3$—CH=$CF_2$

HFO-1225ye: E/Z-1,2,3,3,3-pentafluoropropene or $CF_3$—CF=CHF

HCFO-1232xf: 3,3-difluoro-1,3-dichloropropene or $CClF_2$—CCl=$CH_2$

HFO-1243zf: 3,3,3-trifluoropropene or $CF_3$—CH=$CH_2$.

According to one more particular embodiment, the composition according to the invention may comprise a ternary mixture, for example a mixture chosen from:

HFO-1234yf, HFC-152a, HFC-245cb
HFO-1234yf, HCC-40, HFC-245cb
HFO-1234yf, HCFC-115, HFC-245cb
HFO-1234yf, HFC-152a, HFC-134a
HFO-1234yf, HCC-40, HFC-134a
HFO-1234yf, HCFC-115, HFC-134a
HFO-1234yf, HFC-152a, HFO-1234ze
HFO-1234yf, HCC-40, HFO-1234ze
HFO-1234yf, HCFC-115, HFO-1234ze
HFO-1234yf, HCC-40, HFC-152a
HFO-1234yf, HCC-40, HCFC-115
HFO-1234yf, HFC-134a, HFO-1234ze
HFO-1234yf, HFC-134a, HFO-1243zf
HFO-1234yf, HFO-1234ze, HFC-134a
HFO-1234yf, HFO-1234ze, HFC-245cb
HFO-1234yf, HFO-1243zf, HFC-245cb
HFO-1234yf, HFO-1243zf, HFC-152a
HFO-1234yf, HFO-1243zf, HCFC-115.

According to one more particular embodiment, the composition according to the invention may comprise a quaternary mixture, for example a mixture chosen from:

HFO-1234yf, HFC-152a, HCC-40, HFC-245cb
HFO-1234yf, HFC-152a, HCC-40, HFO-1234ze.

It would not be outside the scope of the invention if the composition comprises a mixture of more than four compounds.

Another subject of the present invention is a composition comprising the compound HFO-1234yf and at least two compounds chosen from HFO-1234ze, HFC-245cb, HFC-134a, HCFC-115, HFC-152a, HCC-40 and HFO-1243zf.

Preferably, the composition comprises the compound HFO-1234yf, HCC-40 and at least one compound chosen from HFO-1234ze, HFC-134a, HCFC-115, HFC-152a and HFO-1243zf.

Preferably, the composition comprises the compound HFO-1234yf, HFC-134a and at least one compound chosen from HFO-1234ze, HCFC-115, HFC-152a and HFO-1243zf.

Preferably, the composition comprises the compound HFO-1234yf, HFO-1234ze and at least one compound chosen from HFC-245cb, HCFC-115, HFC-152a and HFO-1243zf.

Preferably, the composition comprises the compound HFO-1234yf, HFO-1243zf and at least one compound chosen from HFC-245cb, HCFC-115 and HFC-152a.

The preferred and/or aforementioned compositions may additionally comprise at least one other additional compound chosen from HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd, HFC-245eb, HFC-245fa, HFC-23, HFC-143a, HFC-236fa, HCFC-244bb, HCFC-244db, HFO-1132a, HFO-1223, HFO-1225zc, HFO-1225ye, HCFO-1232xf and HCFO-1224xe.

Irrespective of the embodiment, the compound HFO-1234yf preferably represents at least 99% by weight in the composition and advantageously at least 99.5% by weight.

The composition according to the invention may be obtained from HCC-240db and by using one or more reaction steps.

Thus, HCC-240db may be subjected to a gas-phase reaction step with a fluorinating agent, preferably anhydrous HF, in order to directly give HFO-1234yf, optionally accompanied by intermediate products chosen from HCFO-1233xf, HCFC-243db and HCFO-1233zd. The fluorination reaction may be carried out in the presence of a catalyst and preferably at a temperature between 100° C. and 500° C., more preferably between 200° C. and 450° C. After separation of the HFO-1234yf, in particular by settling followed by distillation, the intermediate product(s) and where appropriate the unreacted HCC-240db may then be recycled to the reaction step.

The composition according to the invention may also be obtained from HCC-240db by means of at least two reaction steps. The first step generally consists in subjecting the HCC-240db to a gas-phase reaction with a fluorinating agent, preferably anhydrous HF, in order to give at least one intermediate product such as HCFO-1233xf. In a second step, the intermediate product reacts with a fluorinating agent, preferably anhydrous HF, in order to give a composition comprising HFO-1234yf and at least one additional compound as described above. At the end of the second step, the composition comprising the HFO-1234yf and at least one additional compound is subjected to a separation and/or purification step.

The two steps may be carried out in the presence of a catalyst, it being possible for the catalyst to be identical or different. These steps may be carried out in one and the same reactor when the reaction is carried out in the gas phase. In this case, the reactor may comprise an upper catalyst bed different from that of the lower bed.

When the preparation is carried out using two reactions steps, the reaction temperature of the first step is generally lower than that of the second step and is preferably between 100° C. and 500° C., more preferably between 200° C. and 450° C.

If necessary, after the aforementioned separation and/or purification step, the stream comprising HFO-1234yf may be subjected to a step of azeotropic distillation and/or of adsorption by activated carbon and/or molecular sieve or to a photochlorination step.

According to one embodiment of the invention, the composition is obtained by a series of reactions (FIG. 1). FIG. 1 illustrates a series of reactions for the production of HFO-1234yf. The series of reactions begins with a hydrofluorination reaction of HCC-240db with hydrogen fluoride to give HCFO-1233xf. The compound HCFO-1233xf may in turn undergo a hydrofluorination reaction to give HFO-1234yf. The compound HFO-1234yf may in turn undergo a hydrofluorination reaction to give HFC-245cb. Multitudes of products may be obtained by reactions parallel to this series of reactions for example by isomerization reactions, HCl addition reactions and chlorination reactions.

The reactions described above are preferably carried out in the presence of a supported or unsupported fluorination catalyst, preferably activated in the presence of hydrogen fluoride and/or air, comprising chromium oxides and optionally a co-catalyst based for example on nickel, zinc, titanium, magnesium and tin.

The hydrofluorination reaction(s) may be carried out in the gas phase, optionally in the presence of a sufficient amount of oxygen.

The production of HFO-1234yf may be carried out in one or more reactors in series. The supply of HCC-240db may be placed at the inlet of one of the reactors or at the inlet of the first reactor in series, or at each of the inlets of each of the reactors in series.

The hydrofluorination reaction(s) may be carried out continuously or semi-continuously.

The production of HFO-1234yf may be preferably carried out at an absolute pressure of between 0.1 and 50 bar, more preferably between 0.3 and 15 bar.

The contact time in the reactor is between 1 and 100 seconds, preferably between 5 and 50 seconds.

The molar ratio between the hydrogen fluoride and the organic compounds is between 4:1 and 100:1, preferably between 5:1 and 50:1.

The compositions described according to the invention may contain HF, HCl and inert gases (nitrogen, oxygen, carbon dioxide, carbon monoxide, etc.).

HF and HCl neutralization/elimination steps may also be carried out. The compositions described according to the invention may also contain no, or contain traces of, HF and/or HCl.

In the presence of a large excess of HF used in the reaction step(s), the manufacture of HFO-1234yf may comprise at least one distillation step in order to recover a portion of HF that can be recycled to the reaction step(s).

The compositions according to the invention are of use in many fields of application, especially as heat transfer fluid, propellants, foaming agents, blowing agents, gaseous dielectrics, monomer or polymerization medium, support fluids, agents for abrasives, drying agents and fluids for energy production units.

Embodiments

1. A composition comprising the compound HFO-1234yf and at least one other additional compound chosen from HCFC-240db, HCFO-1233xf, HCFC-243db, HCFO-1233zd, HCC-40, HCFC-114a, HCFC-115, HCFC-122, HCFC-123, HCFC-124, HCFC-124a, HFC-125, HCFC-133a, HCFC-142, HCFC-143, HFC-152a, HCFC-243ab, HCFC-244eb, HFC-281ea, HCO-1110, HCFO-1111, HCFO-1113, HCFO-1223xd and HCFO-1224xe.
2. The composition as in embodiment 1, characterized in that it comprises the compound HFO-1234yf and at least one other additional compound chosen from HCFC-115, HFC-152a and HCC-40, preferably HFC-152a and/or HCC-40.
3. The composition as in embodiment 2, characterized in that it comprises at least one compound chosen from HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd and HCFO-1224xe.
4. The composition as in any one of the preceding embodiments, characterized in that it comprises at least one compound chosen from HFO-1234ze, HFC-245cb, HFC-245eb, HFC-245fa, HFC-23, HFC-134a, HFC-143a, HFC-236fa, HCFC-244bb, HCFC-244db, HFO-1132a, HFO-1223, HFO-1225zc, HFO-1225ye, HCFO-1232xf and HFO-1243zf.
5. The composition as in any one of the preceding embodiments, characterized in that it comprises the compound HFO-1234yf and at least two compounds chosen from HFO-1234ze, HFC-245cb, HFC-134a, HCFC-115, HFC-152a, HCC-40 and HFO-1243zf.
6. The composition as in embodiment 5, characterized in that it comprises the compound HFO-1234yf, HCC-40 and at least one compound chosen from HFO-1234ze, HFC-134a, HCFC-115, HFC-152a and HFO-1243zf.
7. The composition as in embodiment 5, characterized in that it comprises the compound HFO-1234yf, HFC-134a and at least one compound chosen from HFO-1234ze, HCFC-115, HFC-152a and HFO-1243zf.
8. The composition as in embodiment 5, characterized in that it comprises the compound HFO-1234yf, HFO-1234ze and at least one compound chosen from HFC-245cb, HCFC-115, HFC-152a and HFO-1243zf.
9. The composition as in embodiment 5, characterized in that it comprises the compound HFO-1234yf, HFO-1243zf and at least one compound chosen from HFC-245cb, HCFC-115 and HFC-152a.
10. The composition as in any one of embodiments 5 to 9, characterized in that it additionally comprises at least one other additional compound chosen from HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd, HFC-245eb, HFC-245fa, HFC-23, HFC-143a, HFC-236fa, HCFC-244bb, HCFC-244db, HFO-1132a, HFO-1223, HFO-1225zc, HFO-1225ye, HCFO-1232xf and HCFO-1224xe.
11. The composition as in any one of the preceding embodiments, characterized in that it comprises at most 1% by weight of all of the additional compound(s).

The invention claimed is:
1. A composition comprising the compounds HFO-1234yf, HFO-1234ze, and HFO-1243zf, and at least one compound chosen from HCFC-115, HFC-152a, and HCC-40,
   wherein the at least one compound represents at most 1% by weight of the composition, and
   wherein the composition comprises at least 99% by weight of HFO-1234yf.
2. The composition as claimed in claim 1, wherein the composition comprises the compounds HFO-1234yf, HFO-1234ze, HFO-1243zf, and HCC-40 and at least one compound chosen from HFO-1234ze, HFC-134a, HCFC-115, and HFC-152a.
3. The composition as claimed in claim 1, wherein the composition comprises the compounds HFO-1234yf, HFO-

1234ze, HFO-1243zf, and HFC-134a and at least one compound chosen from HCFC-115, and HFC-152a.

4. The composition as claimed in claim 1, wherein the composition comprises the compounds HFO-1234yf, HFO-1234ze, and HFO-1243zf, and at least one compound chosen from HCFC-115, and HFC-152a.

5. The composition as claimed in claim 1, wherein the composition comprises the compounds HFO-1234yf, HFO-1234ze, and HFO-1243zf and at least one compound chosen from HCFC-115 and HFC-152a.

6. The composition as claimed in claim 1, wherein the composition comprises the compound HFO-1234yf, HFO-1234ze, HFO-1243zf, and HCFC-115 and at least one compound chosen from HCC-40, and HFC-152a.

7. The composition as claimed in claim 1, wherein the composition comprises at least 99.5% by weight of HFO-1234yf.

8. A composition consisting of the compounds HFO-1234yf, HFO-1234ze, and HFO-1243zf, and at least one compound chosen from HFC-245cb, HCFC-115, and HFC-152a,
   wherein the at least one compound represents at most 1% by weight of the composition, and
   wherein the composition comprises at least 99% by weight of HFO-1234yf.

* * * * *